United States Patent [19]

Fry

[11] Patent Number: 4,938,209

[45] Date of Patent: Jul. 3, 1990

[54] MASK FOR A NEBULIZER

[76] Inventor: William J. Fry, 122 Ford Hill Rd., Seymour, Tenn. 37865

[21] Appl. No.: 296,011

[22] Filed: Jan. 12, 1989

[51] Int. Cl.$^5$ .................. A61M 16/06; A61M 15/00; A62B 7/00

[52] U.S. Cl. .................. 128/200.21; 128/203.12; 128/203.29

[58] Field of Search ............ 128/203.29, 204.11, 128/203.12, 205.25, 206.21, 206.27, 207.28, 207.11, DIG. 26, 912, 200.14, 200.15, 200.16, 200.17, 200.18, 200.19, 200.21, 200.22, 200.23, 200.24

[56] References Cited

U.S. PATENT DOCUMENTS

| | | | |
|---|---|---|---|
| 1,109,318 | 9/1914 | Browne et al. | 128/203.29 |
| 3,236,236 | 2/1966 | Hudson | 128/207.17 |
| 3,824,999 | 7/1974 | King | 128/207.17 |
| 3,978,854 | 9/1976 | Mills, Jr. | 128/912 |
| 4,274,406 | 10/1984 | Bartholomew | 128/206.21 |
| 4,461,292 | 7/1984 | Montalbano | 128/204.17 |

FOREIGN PATENT DOCUMENTS

| | | | |
|---|---|---|---|
| 0234746 | 9/1987 | European Pat. Off. | 128/200.24 |
| 0266529 | 5/1988 | European Pat. Off. | 128/200.24 |
| 2007789 | 5/1979 | United Kingdom | 128/912 |

Primary Examiner—Edgar S. Burr
Assistant Examiner—Kimberly L. Asher
Attorney, Agent, or Firm—Pitts and Brittian

[57] ABSTRACT

A mask for nebulizer cup or other nebulizing apparatus. The mask (10) comprises a body (14) defining a rearwardly opening cavity (20) for receiving at least a portion of the face of a patient, and defining a forwardly disposed opening (26) communicating with the cavity (20). A delivery conduit (16) is also provided for establishing fluid communication between the outlet (40) of the nebulizer cup (12) and the opening (26) of the body (14). Further, the conduit (16) is rotatably secured to the body (14) at the opening (26) by a ball and socket connecting means (18).

7 Claims, 2 Drawing Sheets

MASK FOR A NEBULIZER

TECHNICAL FIELD

This invention relates to a mask for communicating with the outlet of a nebulizing apparatus and delivering the mist or spray produced by such nebulizing apparatus to the nose and/or mouth of a patient for inhaling.

BACKGROUND ART

Nebulizers which produce a fine spray or mist have long been used in the treatment of various ailments and in the administration of medication. Moreover, masks have been developed which are connected in fluid communication with nebulizers and which are worn by the patient to more efficiently deliver the spray or mist to the nose and/or mouth of the patient. However, many nebulizing devices, such as a conventional nebulizer cup, require that the nebulizer be maintained in an upright position for proper operation, and, accordingly, when a conventional mask is used with the nebulizer, the patient must be in an upright position to maintain the nebulizer in an upright position. Whereas this poses no great problem where the patient is ambulatory, due to medical or physical reasons, many patients are unable to orient their bodies in the position necessary to maintain the nebulizer in the desired position. Certain masks heretofore introduced are disclosed in U.S. Letters Patent Nos. 3,236,236, 3,824,999, 4,274,406 and 4,461,292.

Therefore, it is an object of the present invention to provide an improved mask for communicating with the outlet of a nebulizer and delivering the mist or spray produced by the nebulizer to the nose and/or mouth of a patient for inhaling.

Another object of the present invention is to provide a mask for a nebulizer in which the position of the mask can be selectively altered while the nebulizer is maintained in the desired upright position.

A further object of the present invention is to provide a mask for a nebulizer which is inexpensive to manufacture and maintain.

DISCLOSURE OF THE INVENTION

Other objects and advantages will be accomplished by the present invention which provides a mask for communicating with the outlet of a nebulizer cup or other nebulizing apparatus, and delivering the mist or spray produced by the nebulizer cup to the nose and/or mouth of a patient. The mask generally comprises a body defining a rearwardly opening cavity for receiving at least a portion of the face of the patient and defining a forwardly disposed opening communicating with the cavity. The mask also includes a delivery conduit for establishing fluid communication between the outlet of the nebulizer cup and the opening in the body whereby mist or spray is communicated to the cavity. The delivery conduit has first and second end portions and defines a passageway therethrough. The first end portion of the conduit is rotatably connected to the body with a ball and socket connecting means such that the attitude of the conduit relative to the attitude of the body can be selectively altered. The second end portion of the conduit engages the outlet of the nebulizer cup in order to connect the passageway in fluid communication therewith.

BRIEF DESCRIPTION OF THE DRAWINGS

The above-mentioned features of the present invention will become more clearly understood from the following detailed description of the invention read together with the drawings in which.

BEST MODE FOR CARRYING OUT THE INVENTION

An improved mask for a nebulizer incorporating various features of the present invention is illustrated generally at 10 in the figures. The mask 10 is designed to be received over the face of a patient, and is connected to a nebulizing apparatus such as the illustrated nebulizer cup 12. As will be understood by those skilled in the art, nebulizers, such as the cup 12, are designed to atomize a liquid such as a liquid medication to produce a fine spray or mist which is inhaled. The mask 10 serves as a means for delivering the spray or mist to the nose and/or mouth of the patient.

Figure 2:
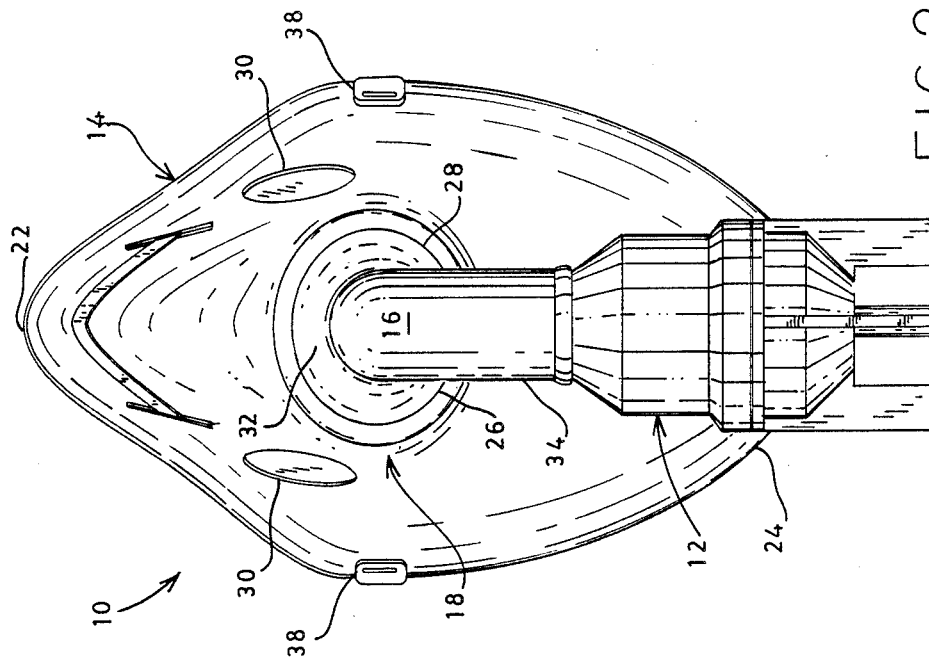
FIG. 2 illustrates a front view of a mask of the present invention.
Figure 1:
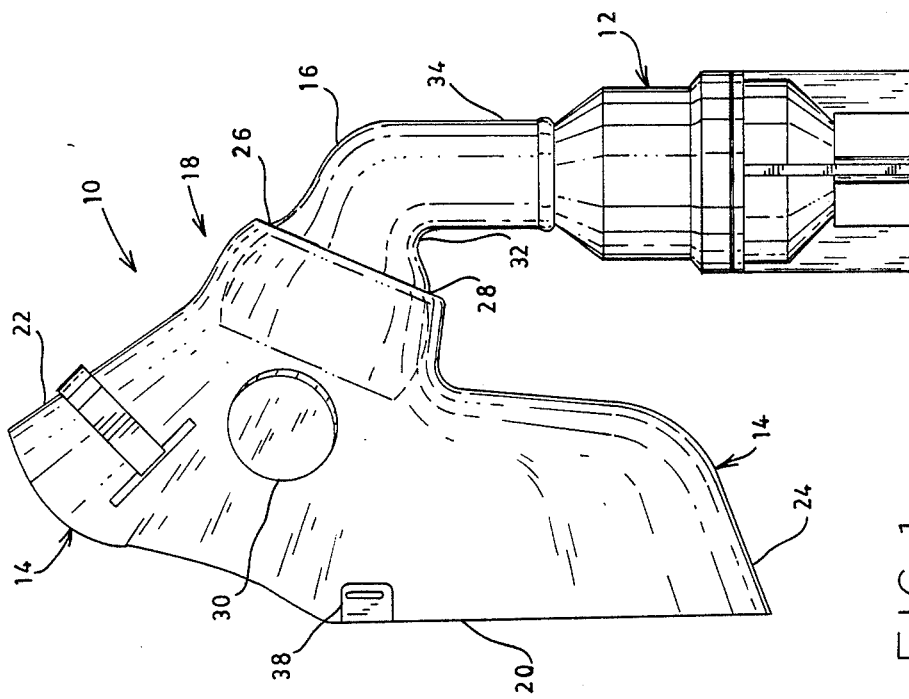
FIG. 1 illustrates a side elevation view of a mask of the present invention.
Figure 3:
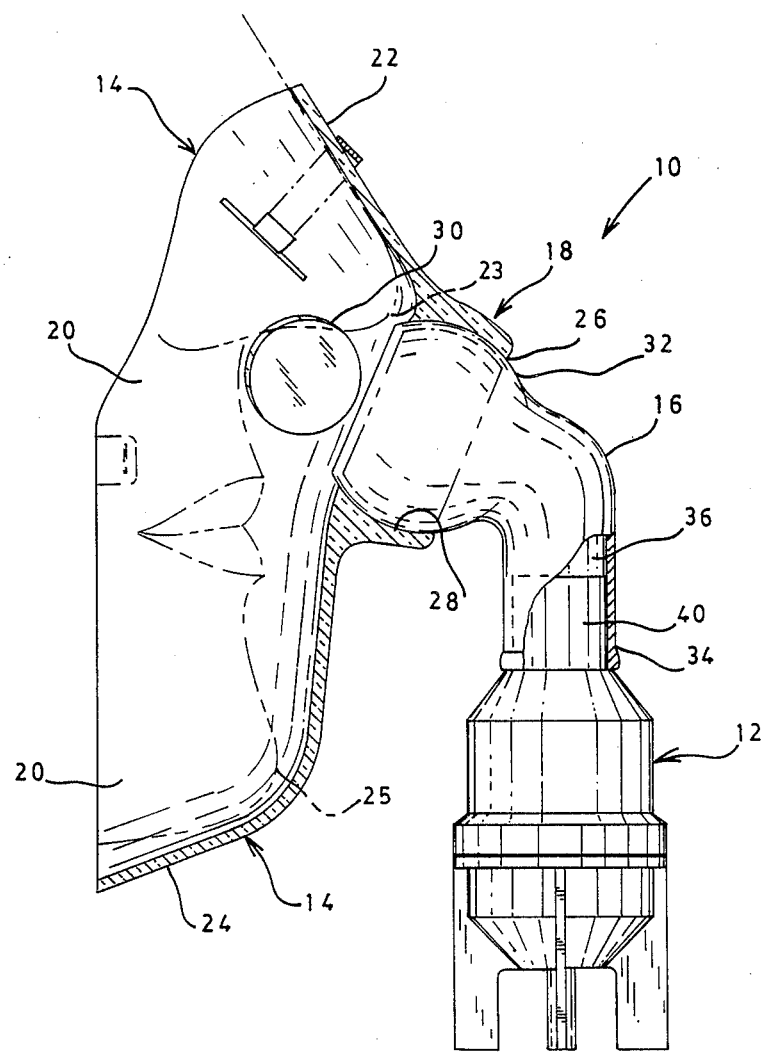
FIG. 3 illustrates a side elevation view, partially in section, of a mask of the present invention.

The mask 10 includes a body 14 and a delivery conduit 16 for connecting the body 14 in fluid communication with the nebulizer cup 12, with a ball and socket connecting means 18 being provided for rotatably connecting the delivery conduit 16 to the body 14. More specifically, the mask body 14 defines a rearwardly opening cavity 20 for receiving the face of the patient, with the upper portion 22 of the body 14 being received over the bridge of the nose 23 and the lower portion 24 of the body 14 being received over the chin 25, as illustrated in FIG. 3. The body 14 is also provided with a forwardly disposed opening 26 which, in the preferred embodiment, defines concaved annular sidewalls such that the opening 26 defines a socket 28 for receiving the conduit 16. As illustrated, the opening 26 communicates with the cavity 20 and is disposed such that when the mask 10 is worn, the opening 26 is oriented just below and forward of the nose 23 of the patient. Of course, this disposition of the opening 26 facilitates delivery of the mist or spray to both the nose and mouth of the patient. It will also be noted that the body 14 can be provided with further openings 30 to ventilate the cavity 20 to insure that the patient's intake of oxygen is sufficient.

The delivery conduit 16 defines a tubular member having first and second end portions 32 and 34, respectively, and a passageway 36 therethrough for communicating mist or spray to the cavity 20. In the preferred embodiment, the first end portion 32 defines a ball-like configuration which is rotatably received in the socket 28. Thus, it will be recognized by those skilled in the art that the conduit 16 is capable of complete rotation about the axis of the opening 26 and angular movement within a selected range with respect to such axis. Further, the second end portion 34 is designed to releasably engage the outlet 40 of the nebulizer cup 12. For example, in the illustrated embodiment, the outlet 40 defines a sleeve which is slidably received in the passageway 36. Therefore, as mist or spray is emitted from the outlet 40, it is carried via the passage 36 to the cavity 20 where it is inhaled by the patient.

In the preferred embodiment, the body 14 is fabricated from a flexible material such as rubber, or a flexible plastic, so as to fit closely and comfortably about the face of the patient, and such that the socket 28 is sufficiently flexible to allow force-fit reception of the ball-like first end portion 32 of the conduit 16. Accordingly, the conduit 16 releasably engages the body 14 such that the mask 10 can be disassembled for cleaning and storage. Preferably, the conduit 16 is made of a strong durable plastic which need not be flexible in view of the wide range of motion conveyed to the conduit 16 by the ball and socket connecting means 18. Moreover, in the preferred embodiment, the fabricating materials for both the body 14 and the conduit 16 are transparent such that the mist or spray produced by the nebulizer cup 12 can be seen through the body 14 and conduit 16 in order to monitor the production and communication of the spray or mist. The above notwithstanding, it will be understood that various alternative fabricating materials can be utilized if desired.

In light of the above, it will be recognized that the present invention provides an improved mask for a nebulizer with great advantages over the prior art. The ball and socket connecting means 18 allows the nebulizer cup 12 to be maintained in the desired upright position notwithstanding the attitude of the body of the patient. For example, a bedridden patient can utilize the mask 10 without sitting or standing erect. Even where the patient is in a prone position, the patient's head can be turned to the side and the conduit 16 rotated to a position whereby the nebulizer cup 12 is in an upright position. Further, the mask 10 can be provided with the oppositely disposed fasteners 38 for engaging the opposite ends of a support strap (not shown) which is received about the head of the patient such that the mask maintains its position without being held in place by the patient or caretaker. Moreover, the relative positions of the nebulizer cup 12 and the body 14 of the mask 10 can be altered during administration of the mist or spray, thus, allowing changes in patient body attitude during the procedure while maintaining the upright position of the nebulizer cup 12.

While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A face mask providing fluid communication between an outlet of an apparatus for nebulizing medication and said face mask, delivering mist or spray produced by said nebulizing apparatus to the nose and/or mouth of a patient wearing said face mask, and having means for maintaining said nebulizing apparatus in an upright position to avoid spillage, said face mask comprising:
    a body defining a rearwardly opening cavity for receiving at least a portion of the face of a patient and also defining a forwardly disposed opening communicating with said cavity;
    a delivery conduit for establishing fluid communication between said outlet of said nebulizing apparatus and said forwardly disposed opening of said body, said conduit having first and second end portions and defining a passageway therethrough;
    said means for maintaining said nebulizing apparatus in a vertical position comprising a ball and socket connecting means rotatably connecting said delivery conduit to said body, whereby said passageway is in fluid communication with said cavity of said body; and
    attaching means for releasably attaching said nebulizing apparatus to said delivery conduit.

2. The mask of claim 1 wherein said ball and socket connecting means forming said means for maintaining said nebulizing apparatus in a vertical position includes a socket defined at said forwardly disposed opening of said body, and a ball-like member provided at said first end portion of said delivery conduit for being rotatably received in said socket.

3. The mask of claim 2 wherein said body defines concaved annular sidewalls circumscribing said forwardly disposed opening of said body whereby said socket is defined.

4. The mask of claim 1 wherein said body defines an upper portion for being received over the bridge of the nose of a wearer of said mask, and a lower portion for being received over the chin of a wearer of said mask.

5. The mask of claim 2 wherein said body is fabricated of a flexible material for releasably securing said delivery conduit to said body.

6. A face mask providing fluid communication between an outlet of an apparatus for nebulizing medication and said face mask, and delivering mist or spray produced by said nebulizing apparatus to the nose and/or mouth of a patient wearing said face mask, and means for maintaining said nebulizer apparatus in a vertical position, said face mask comprising:
    a body defining a rearwardly opening cavity for receiving at least a portion of the face of a wearer of said mask and defining a forwardly disposed opening communicating with said cavity, said body having concaved annular sidewalls circumscribing said opening whereby a socket is defined at said opening; and
    a delivery conduit for establishing fluid communication between said outlet of said nebulizing apparatus and said cavity of said body, said conduit having first and second end portions and defining a passageway therethrough; said means for maintaining said nebulizing apparatus in a vertical position comprising said first end portion of said conduit defining a ball-like configuration rotatably received in said socket of said body whereby said conduit is rotatably secured to said body such that said nebulizing apparatus can be maintained in a vertical position independent of the position of a wearer of said mask, with said passageway in fluid communication with said cavity, and whereby said second end portion releasably engages said outlet of said nebulizing apparatus thereby placing said passageway in fluid communication with said nebulizing apparatus.

7. The mask of claim 6 wherein said body is fabricated of a flexible material for releasably securing said delivery conduit to said body.

* * * * *